United States Patent
Bertsch et al.

(10) Patent No.: US 9,545,238 B2
(45) Date of Patent: Jan. 17, 2017

(54) COMPUTER-AIDED EVALUATION OF AN IMAGE DATASET

(75) Inventors: Rüdiger Bertsch, Erlangen (DE); Roland Brill, Erlangen (DE); Alexander Cavallaro, Uttenreuth (DE); Maria Jimena Costa, Nuremberg (DE); Martin Huber, Uttenreuth (DE); Michael Kelm, Erlangen (DE); Helmut König, Erlangen (DE); Sascha Seifert, Königsbach-Stein (DE); Michael Wels, Bamberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 268 days.

(21) Appl. No.: 13/053,263

(22) Filed: Mar. 22, 2011

(65) Prior Publication Data

US 2011/0235887 A1 Sep. 29, 2011

(30) Foreign Application Priority Data

Mar. 25, 2010 (DE) ........................ 10 2010 012 797

(51) Int. Cl.
*G06F 19/00* (2011.01)
*A61B 6/00* (2006.01)
*A61B 5/055* (2006.01)
*A61B 5/00* (2006.01)

(52) U.S. Cl.
CPC ............ *A61B 6/5217* (2013.01); *A61B 5/055* (2013.01); *A61B 5/4842* (2013.01); *G06F 19/321* (2013.01); *A61B 5/415* (2013.01); *A61B 5/418* (2013.01); *G06F 19/345* (2013.01)

(58) Field of Classification Search
CPC ......... A61B 5/055; A61B 5/415; A61B 5/418; A61B 5/4842; A61B 6/5217; G06F 19/321; G06F 19/345
See application file for complete search history.

(56) References Cited

U.S. PATENT DOCUMENTS

| | | | | |
|---|---|---|---|---|
| 5,779,634 A | * | 7/1998 | Ema et al. | 600/407 |
| 6,714,623 B2 | * | 3/2004 | Sako et al. | 378/98.8 |
| 6,785,410 B2 | * | 8/2004 | Vining et al. | 382/128 |
| 7,689,539 B2 | * | 3/2010 | Sjoblom | G06F 19/321 707/999.002 |
| 7,809,175 B2 | * | 10/2010 | Roehrig | A61B 6/463 382/128 |
| 8,224,046 B2 | * | 7/2012 | Seghers et al. | 382/128 |
| 8,265,728 B2 | * | 9/2012 | MacMahon et al. | 600/407 |
| 2006/0047195 A1 | * | 3/2006 | Shen | 600/407 |
| 2006/0155577 A1 | * | 7/2006 | Niemeyer | G06F 19/321 705/2 |
| 2007/0122018 A1 | * | 5/2007 | Zhou et al. | 382/128 |
| 2007/0127790 A1 | * | 6/2007 | Lau | G06F 17/30265 382/128 |
| 2008/0059245 A1 | * | 3/2008 | Sakaida | G06F 19/321 705/3 |

FOREIGN PATENT DOCUMENTS

DE 102005037374 A1 2/2007
WO WO 03046810 A1 6/2003

OTHER PUBLICATIONS

S. Seifert et al., "Hierachical Parsing and Semantic Navigation of Full Body CT Data", Proceedings of the SPIE, vol. 7259, pp. 725902-725910 (2009); Others; 2009.
German Priority Application DE 10 2010 012 797.3 filed on Mar. 25, 2010 (Not Yet Published).

* cited by examiner

*Primary Examiner* — Katrina Fujita
(74) *Attorney, Agent, or Firm* — Harness, Dickey & Pierce, P.L.C.

(57) ABSTRACT

A method and system for the diagnosis of 3D images are disclosed, which significantly cuts the time required for the diagnosis. The 3D images are for example an image volume dataset of a magnetic resonance tomography system which is saved in an RIS or PACS system. In at least one embodiment, the diagnostic finding are partially automatically generated, and details of the position, size and change in pathological structures are compared to previous diagnostic findings are generated automatically. As a result of this automation the diagnostic work of radiologists is significantly reduced.

14 Claims, 1 Drawing Sheet

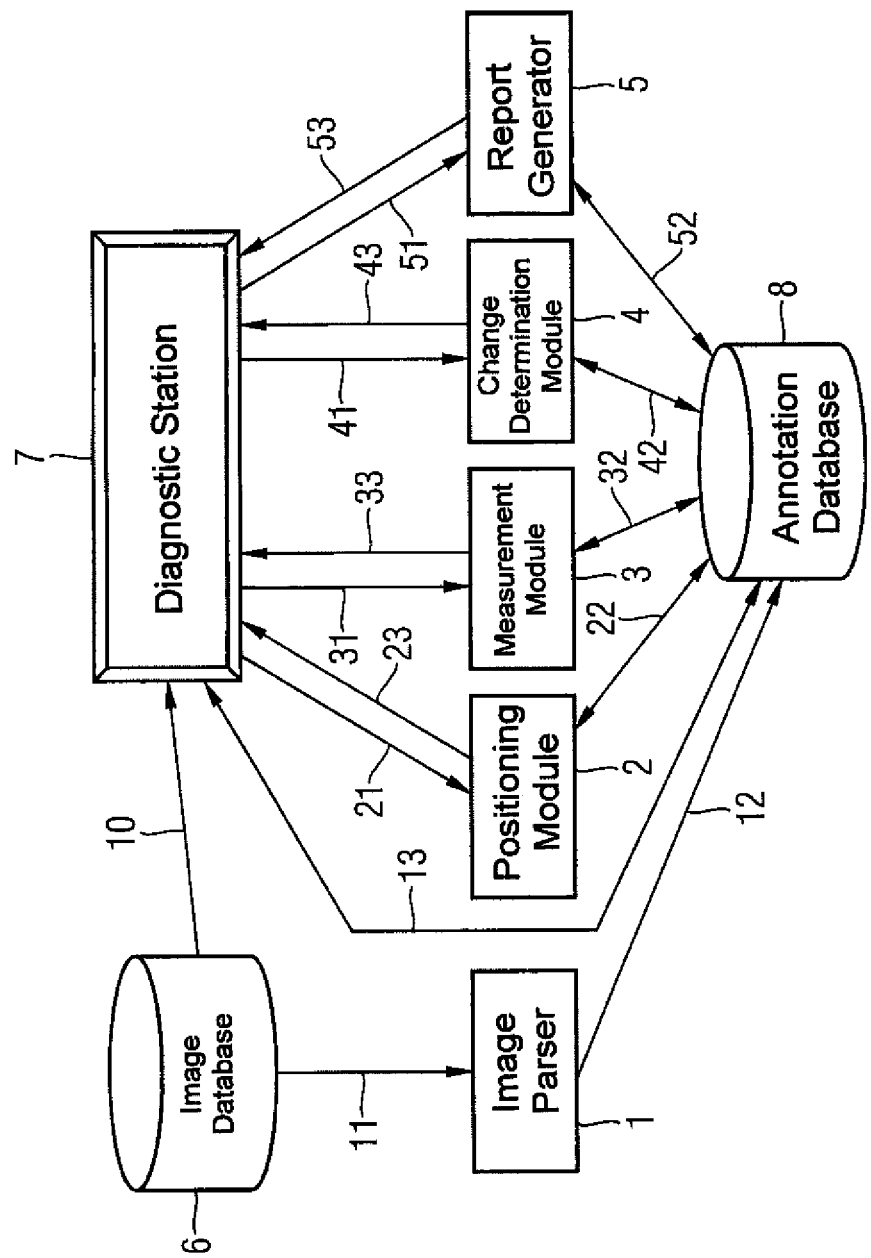

COMPUTER-AIDED EVALUATION OF AN IMAGE DATASET

PRIORITY STATEMENT

The present application hereby claims priority under 35 U.S.C. §119 on German patent application number DE 10 2010 012 797.3 filed Mar. 25, 2010, the entire contents of which are hereby incorporated herein by reference.

FIELD

At least one embodiment of the invention generally lies in the fields of medical engineering and medical informatics and generally relates to the evaluation of an image dataset.

BACKGROUND

The main area of application lies in the field of radiology, in which computer-aided RIS (Radiology Information System) and PACS (Picture Archiving and Communication System) systems are customarily used. The evaluation is here based on an imaging medical examination at different modalities, e.g. a computed tomography system, a magnetic resonance tomography system, a positron emission tomography system, an x-ray device or an ultrasound device. The radiological examination devices mentioned supply the image dataset. The image dataset is generally an image volume dataset containing a volume image, or an image series dataset containing a series of images.

Using modern imaging procedures in medical engineering, image datasets are created, the contents of which are so complex that a full and error-free evaluation by a radiologist is possible only with difficulty. The evaluation of large image datasets is firstly taxing and hence prone to error, and secondly requires great care to be taken during the evaluation, since the evaluation may have consequences for the further treatment of a patient.

Image datasets are nowadays wherever possible evaluated with the aid of computers at diagnostic stations which make it possible to view and navigate through the image dataset and to write up a report (for example as text or dictation). To this end the image dataset is split into series of medical images which a radiologist views essentially sequentially, whereby he dictates the report. The report focuses in particular on describing the appearance, position and changes in pathological structures. The pathological structures may for example be tumors, as well as vessels, bones, etc. which exhibit a pathological deviation compared to a normal healthy state. The diagnostic station here permits navigation through the image dataset, manipulation of the display such as enlarging, measuring and changing the "windowing" (to characterize the structure, and to carry out measurements) as well as a simultaneous display of multiple image datasets in order to determine changes.

For particular examinations there are additionally, besides the form of report described above, what are known as structured diagnostic findings. In this case radiologists fill out a ready-made form. However, in practice this procedure is always very slow, since the radiologists regard it as a limitation and have to avert their eyes from the image datasets in order to fill out the ready-made form. In the type of report described in the introduction this is not the case, since the radiologists can at all times keep the representation of the image datasets in view while they navigate through the image datasets by manually operating a mouse and simultaneously dictate the report.

SUMMARY

In at least one embodiment of the invention, a method and system are provided for the computer-aided evaluation of an image dataset which improves the quality of the report or cuts the time needed to generate the report.

In at least one embodiment, an image dataset is generated using a radiological examination device and is saved in an image database. An evaluation is generated for a pathological structure in the image dataset and is saved in an annotation database. The method of at least one embodiment is characterized in that a positioning module automatically determines a position of the pathological structure in relation to one or more anatomical structures and saves it in the annotation database.

In at least one embodiment, a system comprises an image database in which an image dataset can be saved. The system further comprises an annotation database in which a report can be saved for a pathological structure in the image dataset. The system, in at least one embodiment, is characterized by a positioning module which is equipped for the automatic identification of a position of the pathological structure in relation to one or more anatomical structures.

In at least one embodiment, the invention furthermore comprises a computer-readable data carrier on which is saved a computer program which executes the method just described if it is run in a computer.

In at least one embodiment, the invention furthermore comprises a computer program which is run in a computer and thereby executes the method described above.

The underlying idea of at least one embodiment is that a report is generated partially automatically, in that an indication of the position of the pathological structure is automatically generated. The automatic determination of the position means that a radiologist who generates the report with the aid of a computer does not have to determine and dictate this information himself.

According to a development of at least one embodiment of the method, a previous evaluation for the pathological structure is saved in the annotation database. A change determination module automatically determines a change in the pathological structure in comparison with the previous evaluation and saves it in the annotation database. The advantage of this is that the generation of the report is further automated, in that indications of changes in the pathological structure over time are automatically generated. A radiologist who generates the report does not therefore need to determine and dictate this information himself.

In an additional development of at least one embodiment of the method, a measurement module automatically performs a measurement or calculation of an attribute of the pathological structure in the image dataset and saves the attribute in the annotation database. As a result a further step in the generation of the report is automated, thereby saving the radiologist additional work.

In an embodiment based on the developments described above a report generator automatically combines the determined position of the pathological structure, the determined change in the pathological structure and the determined attribute of the pathological structure and generates therefrom the report in structured form. The advantage of the structured form is that the report can be analyzed by computer, for instance to generate a structured overall diagnostic finding or to automatically output graphs showing developments, for example for the development of a volume of a tumor.

According to one embodiment an image parser automatically looks for and identifies the anatomical structures on the basis of a computerized learning procedure in the image dataset. An identifier of the anatomical structure, a position of the anatomical structure in the image dataset and a segmentation of the anatomical structure are automatically saved in the annotation database for each of the anatomical structures.

In a development of this embodiment a request for the report is first received from an RIS or HIS system (hospital information system) and contains request parameters. An anatomical region is predefined for the report by at least one request parameter. The image parser looks for and identifies only anatomical structures which lie in the anatomical region.

This development is of advantage for example if a full-body CT scan is generated for a patient in an emergency, recording. A request for a report is then received from a hospital information system, wherein a request parameter predetermines the patient's head as the anatomical region for the evaluation, since an internal head injury is suspected. Thanks to the development the identification of the anatomical structures is restricted to the head, thereby also reducing the time needed to generate the report.

The respective modules can be implemented as software modules or hardware modules, especially application-specific integrated circuits or circuit boards.

According to at least one embodiment of a development, the image dataset is an image volume dataset or an image series dataset. The radiological examination device is for example a computed tomography system, a magnetic resonance tomography system, a positron emission tomography system, an x-ray device or an ultrasound device. The report is for example a medical diagnostic finding.

The developments of the embodiments of the method described apply equally for the system. Advantageous embodiments are characterized by the features of the subclaims.

BRIEF DESCRIPTION OF THE DRAWINGS

Example embodiments of the invention are explained in greater detail below on the basis of a FIGURE, which shows:

FIG. 1 an overview of the method and/or the system.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an example embodiment of the invention in the form of an architecture of a software or hardware implementation. A diagnostic station 7 allows a user, in particular a radiologist, user read access 10 to image datasets which are saved in an image database 6. An image parser 1 likewise processes, by way of a read access 11, the image datasets saved in the image database 6. The image parser 1 here identifies anatomical structures in the image datasets.

To this end procedures for computerized learning are used, which are known for example from Seifert, S.; Barbu, A.; Zhou, S. K.; Liu, D.; Feulner, J.; Huber, M.; Suehling, M.; Cavallaro, A., and Comaniciu, D., "Hierarchical parsing and semantic navigation of full body CT data", Medical Imaging 2009: Image Processing, Proceedings of SPIE—Intl. Society for Optical Engineering, Vol. 7259, February 2009, p. 725902-725910, the entire contents of each of which are hereby incorporated herein by reference.

The anatomical structures identified are stored in an annotation database 8 with the aid of a write access 12. An identifier, a position of the anatomical structure in the image dataset and a segmentation of the anatomical structure are here saved for each of the anatomical structures identified. Examples of suitable identifiers include a concept name from RadLex or the FMA ("Foundational Model of Anatomy"). In both cases this relates to ontologies that are suitable for use in radiology.

The results of the image parser 1 are saved in the annotation database 8 in the form of annotations (individual findings from the perspective of a radiologist). The user can access the annotations directly at the diagnostic station 7 via a user read/write access 13, for instance to display names of anatomical structures or associated measurement results. Conversely the user can also add additional annotations manually via the diagnostic station 7.

The processing just described of the image datasets by the image parser 1 can take place beforehand. A user then begins the evaluation of an image dataset. As in the past, the user first navigates to a pathological structure at any position in the image dataset, and selects this for example by clicking with the mouse or touching a screen of the diagnostic station 7 on which the image dataset is displayed. The user then dictates an associated individual finding (for example "multifocal hypodense lesions" or "moderate stenosis"). Alternatively the diagnostic station 7 can offer the user possible diagnostic findings texts for selection, depending on the pathological structure selected, for example via a context menu.

Next the diagnostic station 7 activates—where appropriate on the user's instructions—the positioning module 2 by means of a first module startup 21. The positioning module 2 now automatically determines a position of the selected pathological structure in relation to one or more anatomical structures, especially those that lie in the vicinity of the selected pathological structure. To this end the diagnostic station 7 sends coordinates of the selected pathological structure to the positioning module 2 at the time of the first module startup 21. The positioning module 2 first checks whether the coordinates sent lie within one of the anatomical structures saved in the annotation database 8, and in this case returns the corresponding anatomical structure as a first module response 23. If the coordinates sent do not lie in any of the anatomical structures saved in the annotation database 8, the positioning module 2 returns a relative position of the selected pathological structure to the nearest known anatomical structures as a first module response 23. Corresponding information on the position can be represented by text modules such as "in the liver", "at the height of T4", "in the proximal segment of the right coronary artery" or "anterior to the aorta". Furthermore a plurality of relationships is determined in general for the description of the position in order to define this precisely. The corresponding information is saved as annotations to the image dataset in the annotation database 8 via a first read/write access 22. The automatically determined position of the selected pathological structure is furthermore sent via the first module response 23 to the diagnostic station 7, where if appropriate it is output to the user.

The diagnostic station 7 then performs—where appropriate on the user's instructions—a second module startup 31 of a suitable measurement module 3, depending on the position and type of the selected pathological structure. The measurement module 3 for example implements an algorithm for a quantitative determination of a degree of stenosis if the selected pathological structure is a vessel, or a procedure for automatic volume determination if the selected pathological structure is a lesion. As an alternative to these specialized automatic measurement methods the measurement module 3 can also offer the user of the diagnostic station 7 specialized manual methods for measuring the selected pathological structure. In the latter case the user can add manual measurements. Furthermore the measurement module 3 can also permit other types of evaluation. The measurement results of the measurement module 3 are on the one hand returned as a second module response 33 to the diagnostic station 7, but on the other hand are also saved via a second read/write access 32 in the annotation database 8 as annotations of the image dataset.

The diagnostic station 7 now performs a third module startup 41 of a change determination module 4. The change determination module 4 accesses, via a third read/write access 42, the position determined in the preceding steps as well as the measurement results for the selected pathological structure, which are saved as annotations of the image dataset in the annotation database 8. Alternatively this information can also be sent from the diagnostic station 7 to the change determination module 4 during the third module startup 41. The change determination module 4 checks, with the aid of the third read/write access 42, whether the selected pathological structure has already been described in previous annotations of previous image datasets of examinations of an equivalent patient, which are likewise saved in the annotation database 8, and whether if appropriate any quantitative details are already available there.

For each previous image dataset the entirety of the previous annotations belonging to the previous image dataset here forms a previous evaluation. The change determination module 4 then determines whether the selected pathological structure or a newly determined individual finding for this (i.e. a new annotation) has newly occurred compared to the previous evaluations, or whether the selected pathological structure (if known from previous evaluations) has quantitatively changed, for example has increased or decreased in size. The correspondingly determined changes are output to the diagnostic station 7 and the user with a third module response 43. The user here has the opportunity to have the associated previous annotations displayed in image or text form. In addition the user can also have previous annotations displayed which have no correspondence in the image dataset currently being examined. For each of these previous annotations the user can decide whether to take these over for the current report as well, or whether a comment such as "individual finding X no longer detectable", specifically e.g. "multifocal, hypodense lesions in the liver no longer detectable" should be recorded in the current report.

Finally in a fourth module startup 51 the diagnostic station 7 starts a report generator 5 which automatically combines the determined position of the selected pathological structure, the determined change in the selected pathological structure and the determined quantitative measurement variables of the selected pathological structure and generates the report therefrom. The report is hereby generated in structured form, in that associated individual findings (annotations that relate to the same organ, or bones, lymph nodes or vessels in each case) are listed in a common section. To this end the evaluation generator 5 accesses, via a fourth read/write access 52, the annotation database 8 which contains all individual findings collected for the image dataset currently under consideration, as annotations. The report generated by the report generator 5 is transferred to the diagnostic station 7 as a fourth module response 53 and is saved in the annotation database 8.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for the computer-aided evaluation of an image dataset, comprising:
    generating an unannotated image dataset with the aid of a radiological examination device and saving the image dataset in an image database;
    selecting a pathological structure in the image data set for evaluation;
    generating a report including a description of appearance and position of a pathological structure and changes in the pathological structure in the image dataset and saving the report in an annotation database without user input; and
    automatically determining, via a positioning module, a position of the evaluated pathological structure in relation to one or more anatomical structures and saving the position in the annotation database in an updated report without user input, wherein
        a previous evaluation for the pathological structure is saved in the annotation database,
        automatically determining a change in the pathological structure in comparison of at least one of size and position with the previous evaluation and saving the change in the annotation database without user input,
        at least one of automatically measuring or calculating, via a measurement module, an attribute of the pathological structure in the image dataset based on at least one of a position and a type of the pathological structure and saving the measurement or calculation in the annotation database, and automatically combining the determined position of the pathological structure, the determined change in the pathological structure and the determined attribute of the pathological structure and therefrom generating and outputting a computer analyzable report in a structured form without user input, the report including at least one of diagnostic findings based on the combination of determined position of the pathological structure, the determined change in the pathological structure and the determined attribute of the pathological structure and a graph of changes of pathological structures; and wherein a request for the report is received from a Radiology Information System (RIS) or Hospital Information System (HIS) system and contains request parameters, wherein by way of at least one request parameter an anatomical region in a saved image data set is defined for the evaluation, and wherein an image parser identifies only anatomical structures which lie in the anatomical region and the report is generated for the requested parameter.

2. The method as claimed in claim 1,
wherein the image parser automatically identifies the anatomical structures in the image dataset on the basis of a computerized learning procedure, and
wherein, for each of the anatomical structures, an identifier of the anatomical structure, a position of the anatomical structure in the image dataset and a segmentation of the anatomical structure are automatically saved in the annotation database.

3. The method as claimed in claim 1,
wherein each module is a software module or hardware module.

4. The method as claimed in claim 3,
wherein the hardware module is an application-specific integrated circuit or circuit board.

5. The method as claimed in claim 1,
wherein the image dataset is an image volume dataset or an image series dataset, and
wherein the radiological examination device is a computed tomography system, a magnetic resonance tomography system, a positron emission tomography system, an x-ray device or an ultrasound device.

6. The method as claimed in claim 1,
wherein the report is a medical diagnostic finding.

7. A non-transitory computer-readable data carrier, including a computer program, saved thereon, to execute the method as claimed in claim 1 when run in a computer.

8. A non-transitory computer readable medium including program segments for, when executed on a computer device, causing the computer device to implement the method of claim 1.

9. The method as claimed in claim 1,
wherein a measurement module automatically performs a measurement or calculation of an attribute of the pathological structure in the image dataset and saves the measurement or calculation in the annotation database.

10. The method as claimed in claim 1, further comprising generating a medical diagnosis based on the structured form output from the evaluation generator.

11. A system for the computer-aided evaluation of an image dataset, comprising:

a processor configured to control:

an image database in which an unannotated image dataset is saved;

a diagnostic station including navigation tools configured to allow a user to navigate to and select a pathological structure from the image dataset;

an annotation database in which a report is savable for the pathological structure selected from the image dataset;

a positioning module configured to receive coordinates of the pathological structure from the diagnostic station and automatically determine a position of the pathological structure in relation to one or more anatomical structures and create a report at least partially automatically without user input and save the position information to the annotation database without user input;

a measurement module configured to automatically measure or calculate an attribute of the pathological structure in the image dataset based on at least one of a position and a type of the pathological structure without user input and save the attribute to the annotation database without user input;

a change determination module configured to automatically determine a change in the pathological structure in comparison of at least one of size and position with the saved report without user input and which change is saved in the annotation database as an updated report; and a report generator configured to automatically combine the determined position of the pathological structure without user input, the determined change in the pathological structure and the determined attribute of the pathological structure and automatically generate a computer analyzable report in a structured form from the combined data without user input, the report including at least one of diagnostic findings based on the combination of determined position of the pathological structure, the determined change in the pathological structure and the determined attribute of the pathological structure and a graph of changes of pathological structures, wherein a request for the report is received from a Radiology Information System (RIS) or Hospital Information System (HIS) system and contains request parameters, wherein by way of at least one request parameter an anatomical region in a saved image data set is defined for the evaluation, and wherein an image parser identifies only anatomical structures which lie in the anatomical region and the report is generated for the requested parameter.

12. The system as claimed in claim 11,
wherein the image parser is configured to automatically identify the anatomical structures in the image dataset on the basis of a computerized learning procedure.

13. The system as claimed in claim 11, wherein each module is a software module or a hardware module.

14. The system as claimed in claim 13, wherein the hardware module is an application-specific integrated circuit or circuit board.

* * * * *